United States Patent
Hara et al.

(10) Patent No.: US 11,602,612 B2
(45) Date of Patent: Mar. 14, 2023

(54) SUPPORT SYSTEM, SUPPORT METHOD, AND SUPPORT PROGRAM

(71) Applicant: TERUMO KABUSHIKI KAISHA, Tokyo (JP)

(72) Inventors: Yoshiyuki Hara, Shizuoka (JP); Yuuki Sakaguchi, Shizuoka (JP); Toshio Maki, Shizuoka (JP); Yuusuke Sekine, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 316 days.

(21) Appl. No.: 16/887,637

(22) Filed: May 29, 2020

(65) Prior Publication Data

US 2020/0289787 A1   Sep. 17, 2020

Related U.S. Application Data

(63) Continuation of application No. PCT/JP2018/028726, filed on Jul. 31, 2018.

(30) Foreign Application Priority Data

Nov. 30, 2017   (JP) .............................. JP2017-230855

(51) Int. Cl.
| | |
|---|---|
| *A61M 25/00* | (2006.01) |
| *G16H 40/20* | (2018.01) |
| *G16H 10/60* | (2018.01) |
| *G16H 15/00* | (2018.01) |
| *G16H 50/20* | (2018.01) |
| *G16H 40/40* | (2018.01) |

(Continued)

(52) U.S. Cl.
CPC .... *A61M 25/0009* (2013.01); *A61M 25/0113* (2013.01); *A61M 25/09* (2013.01);
(Continued)

(58) Field of Classification Search
CPC .............. A61M 25/00; A61M 25/0009; A61M 25/0113; G16H 40/20; G16H 40/40;
(Continued)

(56) References Cited

U.S. PATENT DOCUMENTS

| | | |
|---|---|---|
| 2010/0105989 A1 | 4/2010 | Inokuchi et al. |
| 2014/0270423 A1 | 9/2014 | Zellner et al. |
| (Continued) | | |

FOREIGN PATENT DOCUMENTS

| | | | | |
|---|---|---|---|---|
| CN | 107106243 A | * | 8/2017 | ............. A61B 34/00 |
| JP | 2004021380 A | | 1/2004 | |
| (Continued) | | | | |

OTHER PUBLICATIONS

An English Translation of the International Search Report (Form PCT/ISA/210) and the Written Opinion of the International Searching Authority (Form PCT/ISA/237) dated Oct. 9, 2018, by the Japanese Patent Office in corresponding International Application No. PCT/JP2018/028726. (7 pages).

(Continued)

*Primary Examiner* — Edwyn Labaze
(74) *Attorney, Agent, or Firm* — Buchanan Ingersoll & Rooney PC

(57) ABSTRACT

A support system, a support method, and a support program in the form of a non-transitory computer readable medium, which supports selection of a medical instrument and selection of a use form of the medical instrument. A support system includes the data acquisition unit that acquires health care worker data on a health care worker, medical institution data on a medical institution, patient data on a patient, and operation data on a past operation experience of the health care worker, a learning unit that performs machine learning using the health care worker data, the medical institution data, the patient data, and the operation data, and a presentation unit that presents a medical instrument recommended for use in operation on the patient and a recommended use form of the medical instrument based on a result of the machine learning.

17 Claims, 6 Drawing Sheets

(51) Int. Cl.
  *G16H 40/63* (2018.01)
  *A61M 25/01* (2006.01)
  *A61M 25/09* (2006.01)
  *G05B 13/02* (2006.01)
  *G06Q 50/04* (2012.01)

(52) U.S. Cl.
  CPC ......... *G05B 13/0265* (2013.01); *G16H 10/60* (2018.01); *G16H 15/00* (2018.01); *G16H 40/20* (2018.01); *G16H 40/40* (2018.01); *G16H 40/63* (2018.01); *G16H 50/20* (2018.01); *A61M 2025/09108* (2013.01); *A61M 2205/3561* (2013.01); *A61M 2205/50* (2013.01); *A61M 2205/502* (2013.01); *G06Q 50/04* (2013.01)

(58) Field of Classification Search
  CPC ........ G16H 40/63; G16H 10/60; G16H 15/00; G16H 50/20
  USPC .................................................. 604/500–508
  See application file for complete search history.

(56) References Cited

U.S. PATENT DOCUMENTS

| | | | | |
|---|---|---|---|---|
| 2016/0342753 A1* | 11/2016 | Feazell | ................. | G16H 10/60 |
| 2018/0065248 A1* | 3/2018 | Barral | .................... | A61B 34/25 |
| 2018/0182475 A1* | 6/2018 | Cossler | ................. | G16H 50/50 |
| 2019/0163875 A1* | 5/2019 | Allen | ..................... | G16H 10/60 |
| 2019/0279767 A1* | 9/2019 | Bates | ................... | G06V 40/103 |
| 2020/0168334 A1* | 5/2020 | Mowery | ................. | G06N 3/08 |

FOREIGN PATENT DOCUMENTS

| | | |
|---|---|---|
| JP | 2014179092 A | 9/2014 |
| JP | 2017035495 A | 2/2017 |
| WO | 2006132320 A1 | 12/2006 |
| WO | WO-2013126659 A1 * 8/2013 ......... A61B 10/0283 |
| WO | 2016071915 A1 | 5/2016 |
| WO | WO-2017044874 A1 * 3/2017 ............ A61B 1/005 |

OTHER PUBLICATIONS

International Search Report (PCT/ISA/210) dated Oct. 9, 2018, by the Japan Patent Office as the International Searching Authority for International Application No. PCT/JP2018/028726.

Written Opinion (PCT/ISA/237) dated Oct. 9, 2018, by the Japan Patent Office as the International Searching Authority for International Application No. PCT/JP2018/028726.

Office Action (Notice of Reasons for Refusal) dated Jul. 26, 2022, by the Japanese Patent Office in corresponding Japanese Patent Application No. 2019-557006 and an English Translation of the Office Action (10 pages).

* cited by examiner

| MEDICAL INSTITUTION NAME | DOCTOR NAME | OPERATION EXPERIENCE (NUMBER OF TIMES/TIME) | MEDICAL INSTRUMENT PREFERENCE | HABIT OF PROCEDURE | PROCEDURE SUCCESS RATE |
|---|---|---|---|---|---|
| A | O | ×××/××× | △△△△ | ×××× | 85% |
| A | P | ×××/××× | ○○○○ | ×××× | 95% |
| B | Q | ×××/××× | □□□□ | ×××× | 90% |
| A | R | ×××/××× | △△△△ | ×××× | 98% |

| MEDICAL INSTITUTION NAME | STREET ADDRESS | MEDICAL TREATMENT SUBJECT | BED | AMBU-LANCE | MEDICAL INSTRUMENT | CLINICAL PATH | POLICY |
|---|---|---|---|---|---|---|---|
| A | ××× | SURGERY, INTERNAL MEDICINE | 25 | 1 | ×××/×××/××× | SCHEDULE TABLE | ××× |
| B | ××× | OPHTHALMOLOGY | 0 | 0 | ×××/×××/××× | SCHEDULE TABLE | ××× |
| C | ××× | OTOLARYNGOLOGY | 0 | 0 | ×××/×××/××× | SCHEDULE TABLE | ×× |
| D | ××× | OBSTETRICS | 50 | 1 | ×××/×××/××× | SCHEDULE TABLE | ×× |

| IDENTIFI-CATION ID | PATIENT NAME | ADDRESS | AGE | OPERATION HISTORY | HEALTH STATUS | STATE OF TARGET LESION |
|---|---|---|---|---|---|---|
| ××× | S | ××× | 25 | ELECTRONIC MEDICAL RECORD | MEDICAL EXAMINATION RESULT, INTERVIEW RESULT | GOOD |
| ××× | T | ××× | 45 | ELECTRONIC MEDICAL RECORD | MEDICAL EXAMINATION RESULT, INTERVIEW RESULT | NORMAL |
| ××× | U | ××× | 33 | ELECTRONIC MEDICAL RECORD | MEDICAL EXAMINATION RESULT, INTERVIEW RESULT | NORMAL |
| ××× | V | ××× | 8 | ELECTRONIC MEDICAL RECORD | MEDICAL EXAMINATION RESULT, INTERVIEW RESULT | GOOD |

| MEDICAL INSTITUTION NAME | DOCTOR NAME | PATIENT NAME | DISEASE NAME | OPERATION METHOD ADOPTED IN OPERATION | OPERATION TIME | DETAILS OF OPERATION | POST-OPERATION STATUS |
|---|---|---|---|---|---|---|---|
| A | O | S | × × × × | × × × × | × × × × | × × × × | GOOD |
| A | P | T | × × × × | × × × × | × × × × | × × × × | NORMAL |
| B | Q | U | × × × × | × × × × | × × × × | × × × × | CONSULTATION REQUIRED |
| A | R | V | × × × × | × × × × | × × × × | × × × × | NORMAL |

|  | JUNE 1 | JUNE 2 | JUNE 3 |
|---|---|---|---|
| WEATHER | RAIN | RAIN | RAIN |
| TEMPERATURE | 20°C | 17°C | 18°C |
| HUMIDITY | 80% | 75% | 70% |
| SUNSHINE HOURS | 4 HOURS | 3 HOURS | 5 HOURS |

| REGION NAME | POPULATION | FAMILY STRUCTURE | AGE GROUP | MEDICAL HISTORY OR PRESCRIPTION HISTORY IN REGION |
|---|---|---|---|---|
| A | × × × | × × × | 30S | HAVE MEDICAL HISTORY, NO PRESCRIPTION HISTORY |
| B | × × × | × × × | 40S | NO MEDICAL HISTORY, NO PRESCRIPTION HISTORY |
| C | × × × | × × × | 50S | NO MEDICAL HISTORY, NO PRESCRIPTION HISTORY |
| D | × × × | × × × | 40S | HAVE MEDICAL HISTORY, PRESCRIPTION HISTORY |

| IDENTIFI-CATION ID | PATIENT NAME | PRESCRIPTION HISTORY A | PRESCRIPTION HISTORY B |
|---|---|---|---|
| × × × | S | DATE AND TIME, TYPE, AMOUNT, DOSAGE FORM | DATE AND TIME, TYPE, AMOUNT, DOSAGE FORM |
| × × × | T | DATE AND TIME, TYPE, AMOUNT, DOSAGE FORM | DATE AND TIME, TYPE, AMOUNT, DOSAGE FORM |
| × × × | U | DATE AND TIME, TYPE, AMOUNT, DOSAGE FORM | DATE AND TIME, TYPE, AMOUNT, DOSAGE FORM |
| × × × | V | DATE AND TIME, TYPE, AMOUNT, DOSAGE FORM | DATE AND TIME, TYPE, AMOUNT, DOSAGE FORM |

| PROCEDURE | INSURANCE COST | COST OF MEDICAL EQUIPMENT |
|---|---|---|
| A | ¥····,··· | ¥····,··· |
| B | ¥····,··· | ¥····,··· |
| C | ¥····,··· | ¥····,··· |
| D | ¥····,··· | ¥····,··· |

FIG. 5

```
START
  ↓
S1 | DATA ACQUISITION STEP
  ↓
S2 | LEARNING STEP
  ↓
S3 | PRESENTATION STEP
  ↓
END
```

| PRESENTATION CONTENT: | | SUPERIORITY: | BASIS FOR PRESENTATION: |
|---|---|---|---|
| PRESENTATION OF MEDICAL INSTRUMENT | DEVICE A | HIGH | • HIGH SUCCESS RATE OF OPERATION |
| | DEVICE B | MEDIUM | • HAS BEEN USED IN PAST |
| | DEVICE C | LOW | • CAN LOWER OPERATION COSTS |
| PRESENTATION OF SHAPING | J-SHAPE | HIGH | • CAN REDUCE INVASIVENESS |
| | ANKLE TYPE | MEDIUM | • HAS BEEN ADOPTED IN PAST |
| | STRAIGHT TYPE | LOW | • WORK CAN BE SAVED |
| RESHAPING DEVICE | RECOMMENDED FOR USE | HIGH | • LACK OF SHAPING WORK EXPERIENCE |
| | PARTIALLY RECOMMENDED | MEDIUM | • DETAILS SHOULD BE DONE BY HAND |
| | NOT RECOMMENDED | LOW | • POOR WORKABILITY |
| MANUFACTURING APPARATUS | NOT RECOMMENDED | LOW | • CAN BE USED WITH EXISTING PRODUCTS |
| MANUFACTURING OUTSOURCING | NOT RECOMMENDED | LOW | • CAN BE USED WITH EXISTING PRODUCTS |

SUPPORT SYSTEM, SUPPORT METHOD, AND SUPPORT PROGRAM

CROSS-REFERENCES TO RELATED APPLICATIONS

This application is a continuation of International Application No. PCT/JP2018/028726 filed on Jul. 31, 2018, which claims priority to Japanese Application No. 2017-230855 filed on Nov. 30, 2017, the entire content of both of which is incorporated herein by reference.

FIELD OF THE DISCLOSURE

The present disclosure generally relates to a support system, a support method, and a support program.

BACKGROUND DISCUSSION

As an elongated shaped medical instrument (for example, guide wire, guiding catheter, or microcatheter) used in a catheterization procedure such as percutaneous coronary intervention (PCI), a health care worker such as a doctor (hereinafter, referred to as a doctor) selects a medical device having a desired shape that is considered suitable for the procedure from among the medical devices distributed on the market, or the doctor selects a medical device having a desired shape (profile) that is considered to be suitable for the procedure from those that are present, or the doctor himself shapes the medical device into a desired shape. For example, as described in Japanese Patent Application Publication No. 2017-35495, a guide wire may have a distal portion shaped into a J-shape or the like depending on a treatment target site of a patient and a path of a biological lumen to the treatment target site.

The selection of the use form (for example, shape) of the medical instrument is performed based on a theory of a textbook or an empirical rule of the doctor himself. A doctor with relatively little experience with an operation may not have sufficient experience to select a use form (for example, a shape) of a medical instrument. Therefore, it can be a great task for a doctor to determine the use form of the medical instrument according to the contents of the operation. In addition, the selection of the use form of the medical instrument by the doctor itself can have a relatively great influence on the success rate of the operation. As such, a doctor with relatively little experience in the catheterization procedure may avoid the catheterization procedure. This is one of the factors that can hinder the spread of the catheterization procedure.

On the other hand, even if a doctor has a lot of experience in a catheterization procedure, it can be difficult to accurately grasp the state of the biological lumen such as a blood vessel and the state of the biological lumen each time the operation is performed, and it can also be very difficult to determine the most appropriate use form of a medical instrument for operation.

SUMMARY

A support system, a support method, and a support program are disclosed for supporting selection of a medical instrument and selection of a use form of the medical instrument.

A support system is disclosed that is configured to present a medical instrument to be used for an operation to a health care worker, the system including: a data acquisition unit configured to acquire health care worker data on the health care worker, medical institution data on a medical institution, patient data on a patient, and operation data on a past operation experience of the health care worker; a learning unit configured to perform machine learning using the health care worker data, the medical institution data, the patient data, and the operation data; and a presentation unit that presents a medical instrument recommended for use in operation on the patient and a recommended use form of the medical instrument based on a result of the machine learning.

A support method is disclosed that presents a medical instrument to be used for an operation to a health care worker, the method including: acquiring health care worker data on the health care worker, medical institution data on a medical institution, patient data on a patient, and operation data on a past operation experience of the health care worker; performing machine learning using the health care worker data, the medical institution data, the patient data, and the operation data; and presenting a medical instrument recommended for use in operation on the patient and a recommended use form of the medical instrument based on a result of the machine learning.

A non-transitory computer readable medium (CRM) storing computer program code executed by a computer processor that executes a process of presenting a medical instrument to be used for an operation to a health care worker is disclosed, the process comprising: acquiring health care worker data on the health care worker, medical institution data on a medical institution, patient data on a patient, and operation data on a past operation experience of the health care worker; performing machine learning using the health care worker data, the medical institution data, the patient data, and the operation data; and presenting a medical instrument recommended for use in operation on the patient and a recommended use form of the medical instrument based on a result of the machine learning.

The present disclosure presents a medical instrument recommended for use in an operation on a patient and a recommended use form of the medical instrument based on the result of machine learning. By referring to the presented contents, the health care worker can rather easily select a medical instrument suitable for an operation and a use form of the medical instrument suitable for the operation, and the success rate of the operation using the medical instrument can be improved.

BRIEF DESCRIPTION OF THE DRAWINGS

FIG. 4A is a diagram illustrating health care worker data of the support system according to the embodiment disclosed here.

FIG. 4B is a diagram illustrating medical institution data of the support system according to the embodiment disclosed here.

FIG. 4C is a diagram illustrating patient data of the support system according to the embodiment disclosed here.

FIG. 4D is a diagram illustrating operation data of the support system according to the embodiment disclosed here.

FIG. 4E is a diagram illustrating weather data of the support system according to the embodiment disclosed here.

FIG. 4F is a diagram illustrating regional data of the support system according to the embodiment disclosed here.

FIG. 4G is a diagram illustrating prescription data of the support system according to the embodiment disclosed here.

FIG. 4H is a diagram illustrating cost data of the support system according to the embodiment disclosed here.

FIG. 5 is a flowchart illustrating a support method according to the embodiment disclosed here.

FIG. 6 is a diagram exemplifying presentation contents and a basis of presentation illustrated by the support system according to the embodiment disclosed here.

DETAILED DESCRIPTION

Figure 1:
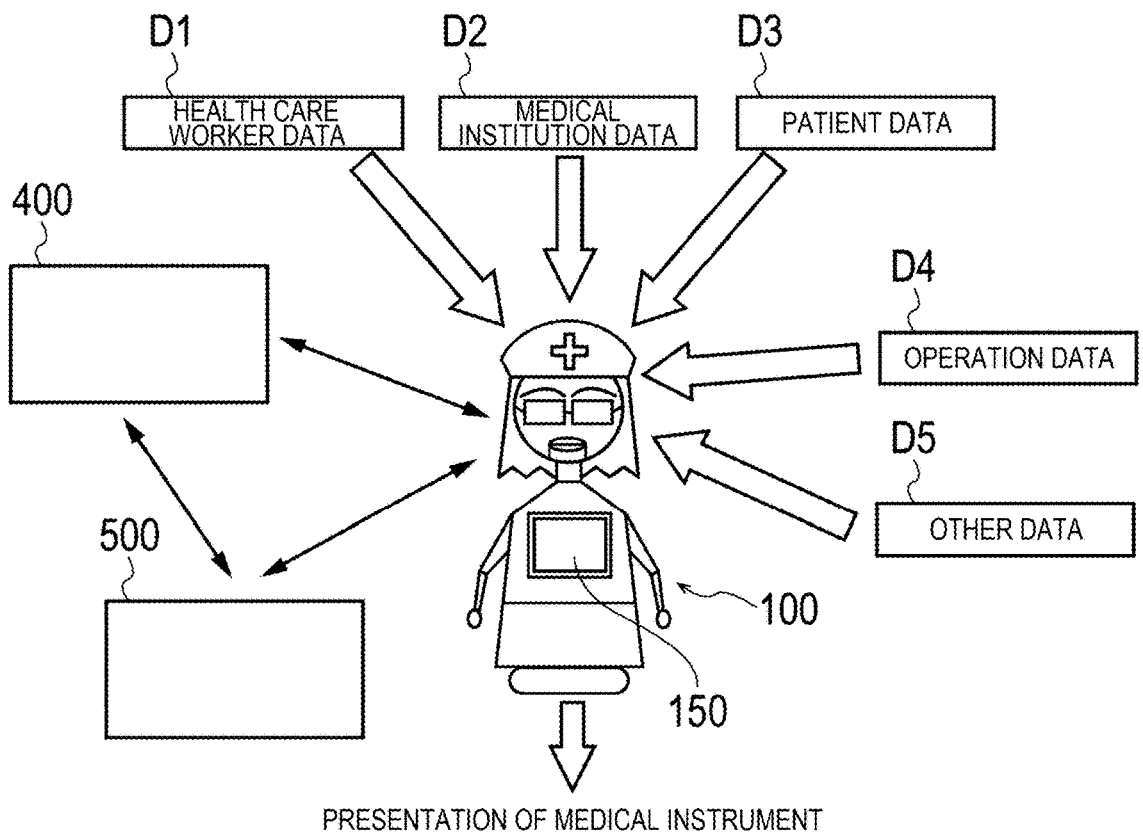
FIG. 1 is a diagram illustrating an outline of a support system according to an embodiment disclosed here.

Set forth below with reference to the accompanying drawings is a detailed description of embodiments of a support system, a support method, and a support program representing examples of the inventive support system, support method, and support program disclosed here. Note that, in the description of the drawings, the same elements will be denoted by the same reference symbols, without redundant description. In addition, the dimensional ratios in the drawings are exaggerated for convenience of explanation, and may differ from actual ratios.

Figure 2:
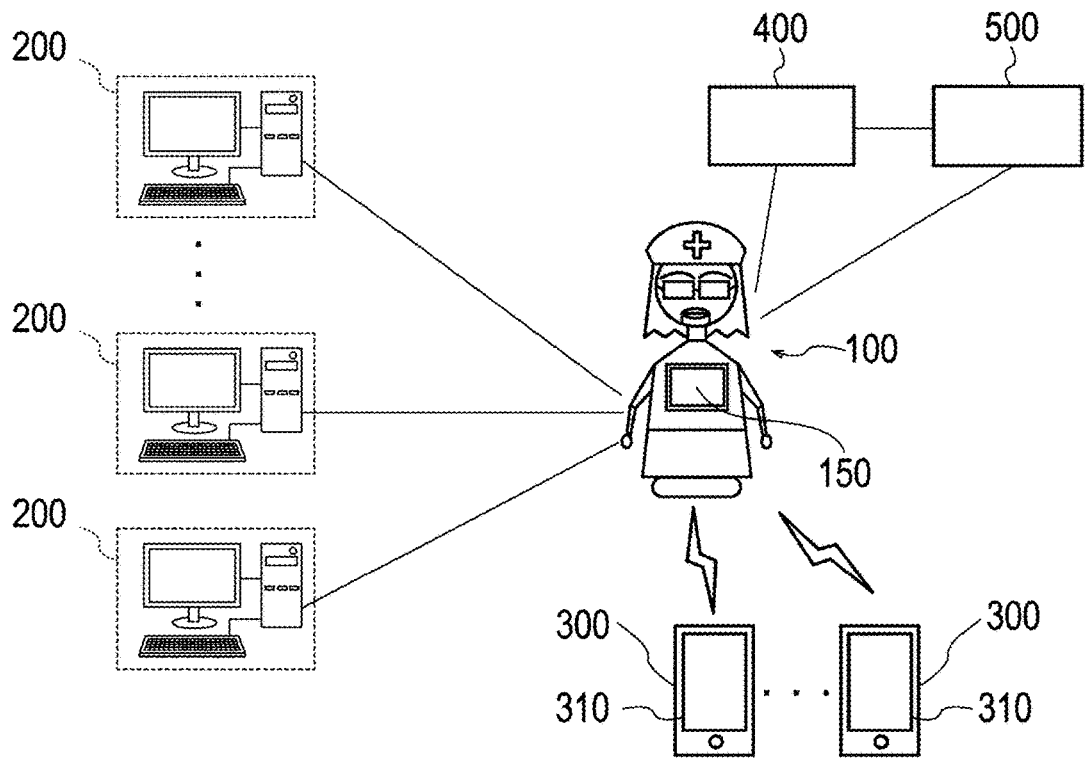
FIG. 2 is a diagram illustrating a network configuration of the support system according to the embodiment disclosed here.
Figure 3A:
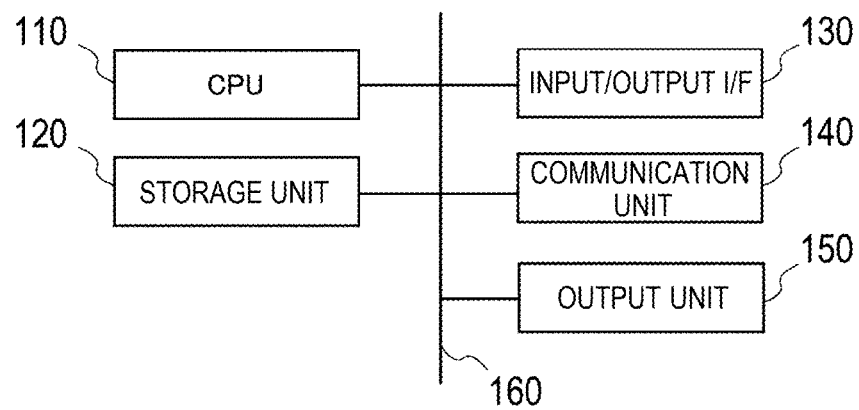
FIG. 3A is a block diagram illustrating a hardware configuration of the support system according to the embodiment disclosed here.
Figure 3B:
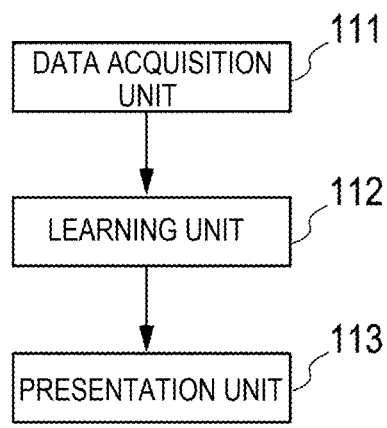
FIG. 3B is a block diagram illustrating a functional configuration of the support system according to the embodiment disclosed here.

FIGS. 1 and 2 are diagrams for explaining an overall configuration of a support system 100 according to the present embodiment. FIGS. 3A and 3B are diagrams provided for describing each unit of the support system 100. FIGS. 4A to 4H are diagrams for explaining data handled by the support system 100.

As shown in FIG. 1, the support system 100 is a system that presents a medical instrument recommended in an operation and a recommended use form (for example, shape, size, hardness, presence or absence of coating, and the like) of the medical instrument using health care worker data D1, medical institution data D2, patient data D3, operation data D4, other data D5 (weather data D51, regional data D52, prescription data D53, cost data D54) and the like. Note that the "medical institution" is not particularly limited, but refers to, for example, a facility where a doctor performs an operation on a patient, and can include a hospital, a clinic, and the like. The "specific (constant) region" is not particularly limited, but is, for example, a region divided by a municipal unit, a prefecture unit, or a country unit.

As shown in FIG. 2, the support system 100 is connected to a medical institution terminal 200 of each medical institution and a patient terminal 300 owned by a patient via a network. The support system 100 is also connected to a shaping device 400 and a manufacturing apparatus 500, which will be described later, via a network. In accordance with an embodiment, the shaping device 400 and the manufacturing apparatus 500 are connected to each other via a network. The support system 100 has a function as a server that transmits and receives data to and from the medical institution terminal 200, the patient terminal 300, the shaping device 400, and the manufacturing apparatus 500.

The network can adopt, for example, a wireless communication method using a communication function such as WiFi® or Bluetooth®, other non-contact wireless communication, or wired communication.

In the present embodiment, the support system 100 is composed of an interactive device capable of communicating with a person through an interaction. As the interactive device, for example, a robot equipped with an artificial intelligence (AI) capability and having an interactive function can be used. The interactive device includes an output unit 150 provided with a display capable of displaying a still image or a moving image and a speaker capable of outputting voice, music, and the like. Note that the interactive device can be equipped with a camera function capable of capturing a still image or a moving image. Further, the appearance design and the like of the interactive device are not particularly limited, and examples of the appearance of the interactive device can include, for example, a human type and an animal type.

Hereinafter, the support system 100 will be described in detail.

The hardware configuration of the support system 100 will be described.

The support system 100 is not particularly limited, but can be composed of, for example, a mainframe or a computer cluster. As shown in FIG. 3A, the support system 100 includes a central processing unit (CPU) 110, a storage unit 120, an input/output interface (input/output I/F) 130, a communication unit 140, and an output unit 150. The CPU 110, the storage unit 120, the input/output I/F 130, the communication unit 140, and the output unit 150 are connected to a bus 160, and transmit and receive data and the like to and from each other via the bus 160.

The CPU 110 is configured to control each unit and executes various arithmetic processes according to various programs stored in the storage unit 120.

The storage unit 120 can include a read only memory (ROM) for storing various programs and various data, a random access memory (RAM) for temporarily storing programs and data as a work area, and a hard disk for storing various programs and various data including an operating system (OS).

The input/output I/F 130 is an interface for connecting input devices such as a keyboard, a mouse, a scanner, and a microphone and output devices such as a display, a speaker, and a printer.

The communication unit 140 is an interface for communicating with the medical institution terminal 200, the patient terminal 300, the shaping device 400, and the manufacturing apparatus 500.

The output unit 150 is configured to output the presentation content presented by the support system 100. The output unit 150 can be composed of, for example, a display and a speaker.

Next, main functions of the support system 100 will be described.

The storage unit 120 is configured to store various types of data such as health care worker data D1 regarding health care workers, medical institution data D2 regarding medical institutions, patient data D3 regarding patients, operation data D4 regarding past operation experiences of health care workers, and other data D5. Further, the storage unit 120 can be configured to store a support program for providing a support method according to the present embodiment.

As illustrated in FIG. 3B, the CPU 110 functions as a data acquisition unit 111, a learning unit 112, and a presentation unit 113 by executing the support program stored in the storage unit 120.

The data acquisition unit 111 and each data will be described.

The data acquisition unit 111 is configured to acquire the health care worker data D1, the medical institution data D2, the patient data D3, the operation data D4, and the other data D5.

As shown in FIG. 4A, the health care worker data D1 can include, for example, the name of the medical institution to which the doctor who is to perform the operation belongs, the doctor's name, the doctor's operation experience (for example, the number of operations performed in the past and the total time of operations performed in the past), the type and name of medical instrument (medical equipment) that the doctor prefers to use, and the habit of the doctor when performing an operation (how to use medical instrument, skilled or unskilled work), and data on the success rate of past operations and the like.

As shown in FIG. 4B, the medical institution data D2 can include, for example, data on the name, address, medical treatment subject, number of equipment such as beds and ambulances, medical instruments, clinical paths, policies, and the like, of the medical institution. Further, the data on the medical instrument can include, for example, data on what kind of medical instrument is stored in the medical institution, and performance (specifications) of the medical instrument stored in the medical institution. In addition, data on the above policies include data on medical policy such as operation policies recommended by each medical institution, medical instruments whose use is restricted at each medical institution, educational policies such as training, and medical policies such as priority medical care. Further, the clinical path data can include, for example, a schedule table that summarizes a schedule from hospitalization to discharge of a plurality of patients.

Note that the medical institution data D2 can also include, for example, data on the layout of the medical institution (data indicating the position and distance of each facility, consultation room, examination room, operation room, nurse station, general ward, intensive care unit (ICU), high care unit (HCU), and the like). The medical institution data D2 can include data on the congestion status of the medical institution. The data related to the congestion status can include, for example, the congestion status of a medical institution within a certain range from the patient's home (congestion status related to outpatients, congestion status related to hospitalization, and the like). For example, when a patient visits a predetermined medical institution, the support system 100 can provide the patient with optimal transportation information (timetable, transfer guidance, and the like) based on data on traffic information and data on congestion status, recommend a doctor, for example, a doctor who has excellent therapeutic results for specific diseases, or present a medical institution where such a doctor works. In addition, the support system 100 may automatically perform a medical appointment reservation or the like in accordance with the arrival time at the medical institution, together with the presentation of the medical institution by means of transportation.

The health care worker data D1 and the medical institution data D2 are stored in the storage unit 120 in a state where the data D1 and D2 are associated with each other, for example.

As shown in FIG. 4C, the patient data D3 can include, for example, the identification ID of the patient (for example, data that can be acquired from personal identity number or the like), the patient's name, address, age, operation history, health status, and the status of target lesion to be operated on. The data regarding the operation history, the health status, and the status of target lesion can be acquired from, for example, an electronic medical record. For example, when the operation target is a blood vessel, the data on the status of target lesion can include data on the running state (i.e., appearance) of the blood vessel. As the data on the running state of the blood vessel, a diagnostic image (imaging data, a CT image, an MRI image, or the like obtained by a catheter for image diagnosis) acquired by an examination using various medical devices performed prior to an operation can be used. Note that, the patient data D3 can also include data on the past medical history, the family structure, the results of the medical examination (height, weight, blood pressure), and the like.

Note that, the patient data D3 may include, for example, data on the genetic information of the patient. The genetic information may include not only the genetic information of the patient but also the genetic information, for example, on a relative. The genetic information can be configured of, for example, a DNA test result or the like. The genetic information can be used, for example, to determine whether a disease may be strongly affected by genetic factors when determining a patient's disease.

Each of the data included in the patient data D3 is stored in the storage unit 120 in a state of being linked to each patient.

As shown in FIG. 4D, the operation data D4 can include data on, for example, the name of a medical institution, the name of a doctor, the name of a patient operated by each doctor, the name of a disease, the operation method adopted in the operation, the operation time, the details of the operation, and the post-operation status. The operation data D4 has a role of complementing the data on the operation included in the health care worker data D1 (see FIG. 4A).

The operation time (operation time of operation) can be used, for example, to evaluate the technical aspects of a doctor. A doctor, for example, determined to have a relatively short operation time and relatively high skill can determine that a certain design error can be allowed for the shape (profile) of the proposed medical instrument.

The details of the operation include, for example, data on treated blood vessel running state and blood vessel state and untreated blood vessel running state and blood vessel state. By referring to this data on the treated blood vessel running state, the blood vessel state, the untreated blood vessel running state, and the blood vessel state, it is possible to obtain data as to whether there is a blood vessel discarded by a doctor (a blood vessel whose treatment or recovery has been abandoned) and data on what each doctor prioritizes in the operation. Further, the details of the operation can include, for example, data when the medical instrument used in one operation is switched. Specifically, the details of the operation can include various data relating to the cause of switching medical instruments such as used together when the switching of the medical instrument (operation time), the state of the patient, the dose of the contrast agent, the imaging time, and the medical instrument used when switching the medical instrument.

The post-operation status can include, for example, data such as the success rate of the operation, the prognosis of the patient, and the lifetime of the patient who has undergone the operation.

The operation data D4 is stored in the storage unit 120 in a state where the operation data D4 is associated with the health care worker data D1 and the medical institution data D2.

Other data D5 to be acquired by the data acquisition unit 111 can include, for example, weather data D51 shown in FIG. 4E, regional data D52 shown in FIG. 4F, prescription data D53 shown in FIG. 4G, and cost data D54 shown in FIG. 4H.

As shown in FIG. 4E, the weather data D51 includes, for example, the weather, temperature, humidity, and sunshine duration of the surrounding environment of each medical institution.

The data acquisition unit 111 can acquire, for example, weather data D51 and regional data D52 from the Internet.

As shown in FIG. 4F, the regional data D52 can include, for example, a specific region name, a population in a specific region, a main family structure in a specific region (for example, an average value of the number of family members in a specific region), an age group in a specific region (for example, an average value of the age group in a specific region), and information on whether the patient has a medical history or a prescription history in the specific region. Note that the regional data D52 can include, for example, data on diseases that are prevalent in the specific region. Note that the regional data D52 can include, for example, data on traffic information in the specific area. The data on traffic information can include, for example, the distance from the patient's home to the medical institution, and the type of available transportation (for example, bus or train).

As shown in FIG. 4G, the prescription data D53 can include, for example, data on a patient identification ID, a patient name, a prescription history A of a drug prescribed at a medical institution, a prescription history B of a drug prescribed at a pharmacy, and the like. The prescription history A can include, for example, data on the date and time of prescription, the type of drug, the prescription amount, the dosage form, and the like. Further, the prescription history B can include data on drugs actually prescribed to the patient at the pharmacy based on the prescription provided by the medical institution. The prescription history B can include, for example, data on the date and time of prescription, the type of drug, the prescription amount, the dosage form, and the like (prescription history and the like described in the drug history handbook). Note that the drug according to the present embodiment includes a so-called digital drug equipped with a digital function (for example, a function of detecting biological information on an organ of a living body after taking the medicine and acquiring the information). For example, the present disclosure can be used for sharing information on a patient acquired by a digital drug with a medical institution, a patient, a health care worker, and the like, and monitoring a patient's medication state.

Each of the data included in the prescription data D53 is stored in the storage unit 120 in a state of being linked to each patient.

As shown in FIG. 4H, the cost data D54 can include, for example, data on the name of the operation, the insurance cost recorded when the operation is performed, and the cost (sales price) of the medical equipment used in the operation.

Further, the other data D5 can include reuse data on medical instruments and drugs. The reuse data can include, for example, information on whether the medical instrument can be reused by performing cleaning or sterilization. The medical instrument is, for example, a single-use medical instrument, but may be a medical instrument (some components of a medical instrument) other than the single-use medical instrument. In addition, the reuse data can include, for example, information on surplus medicine. The surplus medicine can include, for example, information on whether a medicine (for example, a liquid medicine) stored in a predetermined amount in a container such as a bottle can be used for a plurality of patients. For example, when a drug stored in a particular container can be administered to a patient and a drug stored in a similar container can be administered to another patient, the drug is treated as reusable.

Note that the reuse data can be acquired in real time from, for example, a hospital information system of a medical institution that owns a medical instrument or a medicine to be reused.

The data acquisition unit 111 can acquire, for example, medical data as other information useful for supporting a health care worker. As medical data, for example, disease data relating to diseases (disease name, symptoms, necessity of medical treatment, and the like), treatment data relating to treatment (treatment method, period required for treatment, necessary equipment and drugs, and their wholesale prices, and the like), example data on how to use the medical instrument, and the like. The data acquisition unit 111 can acquire, for example, the medical data from the Internet or electronic data of a medical specialty book captured by a scanner or the like.

Next, the learning unit 112 will be described.

The learning unit 112 is configured to perform machine learning using the health care worker data D1, the medical institution data D2, the patient data D3, the operation data D4, and the other data D5. Note that in this specification, "machine learning" refers to analyzing input data using an algorithm, extracting useful rules and determination criteria from the analysis result, and developing the algorithm.

The support system 100 according to the present embodiment presents a recommended medical instrument and a recommended use form of the medical instrument to a doctor. The support system 100 performs machine learning based on the above-described data so that the presentation content does not lack validity.

Specifically, the presentation unit 113 can be configured to display the type, name, model number, and the like of the recommended medical instrument in consideration of the contents of the operation when a request is made by a doctor or a nurse before or during the operation. The presentation unit 113 presents a recommended use form of the medical instrument in consideration of the contents of the operation. Examples of the use form of the medical instrument include the shape of the medical instrument at the time of operation, and in addition to the shape, dimensions, hardness, the presence or absence of a coating, combinations of the shape, the dimensions, the hardness, and/or the presence or absence of the coating, and the like. In the present embodiment, when the medical instrument presented by the presentation unit 113 is a medical instrument having a structure that can be shaped, the presentation unit 113 presents a shape that is one of the use forms. Note that, as a medical instrument (or medical device) having a structure that can be shaped, for example, a guide wire, a guiding catheter, a microcatheter, or the like whose distal portion can be shaped.

When presenting the medical instrument and the use form of the medical instrument, the presentation unit 113 presents the content of the presentation and the grounds of the presentation leading to the presentation. If there are a plurality of grounds, the plurality of grounds can be presented. The doctor can use each presentation content with a sense of consent by being shown the basis for selecting the presentation content together with the medical instrument and the use form of the medical instrument. Note that the method of presenting the basis may, for example, show the relationship between the data using a graph or a table, or may specifically show an event that leads to the basis together with a numerical value such as a contribution rate.

In the present embodiment, the presentation unit 113 is configured to perform the presentation when a presentation request is made by a doctor, a nurse, or the like. However, the timing at which the presentation unit 113 performs the presentation is not particularly limited. For example, the presentation unit 113 may automatically or regularly perform data acquisition before or during an operation, and may automatically perform presentation to the doctor or the like when the content of the presentation is updated even when there is no presentation request from the doctor or the like.

As shown in FIG. 1, a shaping device 400 can be incorporated in the support system 100. The shaping device 400 is a device that shapes a medical instrument on behalf of a doctor or the like. Further, the manufacturing apparatus 500 can be incorporated in the support system 100. In accordance with an embodiment, the manufacturing apparatus 500 is a device that manufactures a medical instrument according to the product specifications (shape, size, hardness, presence or absence of coating) of the medical instrument presented by the presentation unit 113. Note that the support system 100, the shaping device 400, and the manufacturing apparatus 500 may be disposed, for example, in an operation room where a doctor performs an operation, or may be disposed in a place other than the operation room. For example, the manufacturing apparatus 500 may be disposed at an external institution other than a medical institution (for example, a company production facility). When the manufacturing apparatus 500 is disposed in an external institution, the support system 100 can provide learning information to an external institution before performing an operation, for example, and outsource the manufacture of a medical instrument.

FIGS. 5 and 6 are diagrams for explaining the support method according to the present embodiment. Hereinafter, the support method according to the present embodiment will be described with reference to FIGS. 5 and 6.

Generally described with reference to FIG. 5, the support method includes a data acquisition step (S1) of acquiring the health care worker data D1, the medical institution data D2, the patient data D3, the operation data D4, and the other data D5; a learning step (S2) of performing machine learning using the health care worker data D1, the medical institution data D2, the patient data D3, the operation data D4, and the other data D5, and a presenting step (S3) of presenting a medical instrument recommend for use in an operation and a recommended use form of the medical instrument based on a result of the machine learning. Hereinafter, each step will be described.

Note that a machine learning algorithm is generally classified into supervised learning, unsupervised learning, reinforcement learning, and the like. In the supervised learning algorithm, a data set of the input and the result is provided to the learning unit 112 to perform machine learning. In the unsupervised learning algorithm, machine learning is performed by providing a large amount of only input data to the learning unit 112. The reinforcement learning algorithm changes the environment based on the solution output by the algorithm, and makes corrections based on the reward of how correct the output solution is. As the machine learning algorithm of the learning unit 112, for example, supervised learning, unsupervised learning, reinforcement learning, a combination of supervised learning, unsupervised learning and/or reinforcement learning, or the like can be used.

First, the data acquisition step (S1) will be described. In the data acquisition step (S1), the data acquisition unit 111 is configured to acquire the health care worker data D1, the medical institution data D2, the patient data D3, the operation data D4, and the other data D5, and stores the health care worker data D1, the medical institution data D2, the patient data D3, the operation data D4, and the other data D5 in the storage unit 120. For example, when the operation performed by the doctor is PCI (percutaneous coronary intervention), the data acquisition unit 111 acquires various data on the success rate of the previous operation of the doctor, the running state of the patient's coronary artery based on the CT image (the state of the target lesion), the hospital's treatment policy, and the cost of operation.

Next, the learning step (S2) will be described.

In the learning step (S2), the learning unit 112 is configured to apply a predetermined learning algorithm based on the data stored in the storage unit 120. For example, when a supervised learning algorithm is employed, a known algorithm such as a least squares method, a linear regression, an autoregression, or a neural network can be applied.

The learning unit 112 refers to, for example, the operation data D4 and searches for past data that is similar in conditions (disease name, target lesion, state of the target lesion, and the like) to the operation to be performed by the doctor. A plurality of candidates are selected from among the data, and a past success rate, an operation time, a postoperative state of the patient, and the like are weighted. Then, the learning unit 112 can obtain, as a learning result, a medical instrument recommended to be used in the operation performed by the doctor and a candidate for a recommended use form (shape) of the medical instrument.

Further, regarding the medical instrument used for the operation, the learning unit 112 can machine-learn information that contributes to the determination of reuse of a medical device based on information such as whether the medical device is reusable, and if the medical instrument is reusable, what kind of method (washing and sterilization method) is to be adopted to make the medical instrument reusable, and which component of the medical instrument can be reused. Similarly, regarding the drug (or drugs) used for the operation, the learning unit 112 can machine-learn information that contributes to the determination of reuse of a drug based on information such as whether the drug is reusable, and if the drug is reusable, what kind of method (how to store medicines and provide them to patients) is to be adopted to make the drug reusable. The presentation unit 113 can provide a medical institution with information on reuse of medical instruments and drugs by presenting the learning result of the machine learning described above. The medical institution can effectively reduce medical expenses by acquiring or sharing the learning result regarding the reuse between a specific medical institution and/or a plurality of medical institutions.

Next, the presentation step (S3) will be described.

The presentation unit 113 is configured to present the learning result of the learning unit, for example, as shown in FIG. 6. In addition, the presentation unit 113 presents the basis for the presentation together with the presentation content. Note that the presentation content and the basis for the presentation can be presented on, for example, a display of the output unit 150 (see FIG. 1) included in the interactive device 100.

With reference to FIG. 6, an example of the presentation content and the basis for the presentation will be described.

The presentation content can include the type, name, model number, and the like of the medical instrument. In addition, when the presented medical instrument has a structure that can be shaped, a use form recommended in operation is presented. The doctor can improve the success rate of the operation by performing the presented shaping on the medical instrument.

If the presented medical instrument can be shaped, the presentation content indicates whether or not the shaping work by the shaping device 400 is necessary. When the shaping is performed by the shaping device 400, the work by the doctor can be omitted, and an operation using an existing product can be performed.

Further, when the presented medical instrument can be shaped, the presentation content indicates whether or not the manufacturing apparatus 500 needs to perform a manufacturing work of the medical instrument. For example, when shaping by the shaping device 400 is rather difficult, or when shaping by the shaping device 400 can impair (or reduce) product performance (such as a decrease in product strength), it may be preferable to manufacture a new medical instrument. In such a case, by operating the manufacturing apparatus 500 to manufacture a medical instrument, it is possible to provide a product having desired product specifications in terms of shape, dimensions, hardness, presence or absence of coating, and the like. In particular, when an operation is performed using a surgical robot, a medical instrument suitable for the product specifications of the surgical robot can be provided, which can contribute to an increase in the success rate of the operation using the medical instrument.

The doctor can select a medical instrument and a use form of the medical instrument based on the content presented by the support system 100. The doctor performs an operation using the medical instrument. Note that, the support system 100 may capture various data (operation time, success of the operation, and the like) acquired during the operation, and may present new presentation contents during the operation. For example, if the operation is not progressing smoothly, other medical instruments and other use forms can be presented. The doctor can re-select the medical instrument and use form based on the new presentation content.

Various data obtained by the operation performed by the doctor is updated as new data. Then, the learning unit 112 can execute machine learning using the updated data to update the learning model. Based on the updated learning model, the support system 100 performs presentation of a recommended medical instrument and recommended use form of the medical instrument using updated data, for example, when the same doctor performs an operation, when a different doctor performs an operation, and the like, based on the updated learning model.

As described above, the support system 100 according to the present embodiment includes the data acquisition unit 111 that acquires the health care worker data D1 on the health care worker, the medical institution data D2 on the medical institution, the patient data D3 on the patient, and the operation data D4 on the past operation experience of the health care worker, the learning unit 112 that performs machine learning using the health care worker data D1, the medical institution data D2, the patient data D3, and the operation data D4, and the presentation unit 113 that presents a medical instrument recommended for use in operation on a patient and a recommended use form of the medical instrument based on the result of machine learning.

As described above, the support system 100 presents a medical instrument recommended for use in an operation on a patient and a recommended use form of the medical instrument based on the result of machine learning. By referring to the presented contents, the doctor can rather easily select a medical instrument suitable for an operation and a use form of the medical instrument suitable for the operation, and the success rate of the operation using the medical instrument can be improved.

In addition, when the medical instrument has a structure that can be shaped, the presentation unit 113 can present a shape of the medical instrument suitable for operation. Therefore, the doctor can rather easily select the recommended shaping of the medical instrument, and can appropriately improve the success rate of the operation using the medical instrument.

In addition, the support system 100 can include the shaping device 400 for shaping a medical instrument, and the presentation unit 113 can present whether shaping work by the shaping device 400 is necessary when presenting a shape suitable for operation. Then, the shaping device 400 executes shaping of the medical instrument when the presentation unit 113 determines that shaping by the shaping device is necessary. Therefore, the doctor can shape the medical instrument with the shaping device 400, so that the work load required for shaping can be reduced and the doctor can shape the medical instrument to a shape more similar to the presented shape.

In addition, the support system 100 can include the manufacturing apparatus 500 that manufactures a medical instrument, and the presentation unit 113 can determine the whether a manufacturing work by the manufacturing apparatus 500 is necessary when presenting a shape suitable for an operation, and the manufacturing apparatus 500 executes the manufacturing of the shaped medical instrument when it is presented that the manufacturing by the manufacturing apparatus is necessary. Therefore, in cases where the performance of medical instruments deteriorates due to processing such as shaping, it is possible to provide a new product that maintains the product performance, and thereby it is possible to suitably improve the success rate of the operation.

In addition, the presentation unit 113 is configured to present the basis for the presentation together with the presentation content. For this reason, it is possible for a health care worker, a patient, and the like to adopt the presented content with a sense of satisfaction.

In addition, the support method according to the present embodiment includes the data acquisition step (S1) of acquiring the health care worker data D1 on the health care worker, the medical institution data D2 on the medical institution, the patient data D3 on the patient, and the operation data D4 on the past operation experience of the health care worker, the learning step (S2) of performing machine learning using the health care worker data D1, the medical institution data D2, the patient data D3, and the operation data D4, and the presentation step (S3) of presenting a medical instrument recommended for use in operation on a patient and a recommended use form of the medical instrument based on the result of machine learning. Therefore, by referring to the presented contents, the doctor can rather easily select a medical instrument suitable for an operation and a use form of the medical instrument suitable for the operation, and the success rate of the operation using the medical instrument can be improved.

In addition, the support program according to the present embodiment executes the data acquisition step (S1) of acquiring the health care worker data D1 on the health care worker, the medical institution data D2 on the medical institution, the patient data D3 on the patient, and the operation data D4 on the past operation experience of the health care worker, the learning step (S2) of performing machine learning using the health care worker data D1, the medical institution data D2, the patient data D3, and the operation data D4, and the presentation step (S3) of presenting a medical instrument recommended for use in operation on a patient and a recommended use form of the medical instrument based on the result of machine learning. Therefore, by referring to the presented contents, the doctor can rather easily select a medical instrument suitable for an operation and a use form of the medical instrument suitable for the operation, and the success rate of the operation using the medical instrument can be improved.

As described above, the support system, the support method, and the support program according to the present invention have been described through the embodiments. However, the present disclosure is not limited to each configuration described in the specification, but can be appropriately modified based on the description in the claims.

For example, the support system, the support method, and the support program according to the above-described embodiment may share the acquired data and the content of presentation between a plurality of medical institutions, or may be used only by a single medical institution.

Further, if the data used for machine learning according to the present invention may include at least health care worker data, medical institution data on medical institutions, patient data on patients, and operation data on past operating experiences of health care workers. The content to be presented only needs to include at least the medical instrument and the use form of the medical instrument.

In addition, the support system, the support method, and the support program according to the present disclosure can include any medical instruments used for operation, and are not limited to catheters, guide wires, and the like. The operation to be applied is not limited to only the operation using a catheter. The use form of the medical instrument can be, for example, the shape, size, hardness, presence or absence of a coating, and the like, and is not limited to the shape described in the embodiment. Note that when the support system is configured to be able to be presented by the presentation unit for each of the above items other than the shape, for example, the support system may include various devices for adding a desired use form to the medical instrument together with or instead of the shaping device.

The means and method for performing various processes in the support system according to the above-described embodiment can be realized by either a dedicated hardware circuit or a programmed computer. The support program may be provided by a computer-readable recording medium such as a compact disc read only memory (CD-ROM), or may be provided online via a network such as the Internet. In this case, the program recorded on the computer-readable recording medium is usually transferred and stored in a storage unit such as a hard disk. Further, the support program may be provided as independent application software.

The detailed description above describes embodiments of a support system, a support method, and a support program. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A support system configured to present a medical instrument to be used for an operation to a health care worker, the system comprising;
    a data acquisition unit configured to acquire health care worker data on the health care worker, medical institution data on a medical institution, patient data on a patient, and operation data on a past operation experience of the health care worker;
    a learning unit configured to perform machine learning using the health care worker data, the medical institution data, the patient data, and the operation data;
    a presentation unit configured to present a medical instrument recommended for use in operation on the patient and a recommended use form of the medical instrument based on a result of the machine learning, and wherein the presentation unit is configured to present a shape of the medical instrument suitable for the operation when the medical instrument has a structure that can be shaped before the operations;
    a manufacturing apparatus configured to manufacture the medical instrument;
    when presenting the shape suitable for the operation, the presentation unit is configured to present whether a manufacturing work by the manufacturing apparatus is necessary; and
    the manufacturing apparatus is configured to execute the manufacturing of the shaped medical instrument when the presentation unit presents that the manufacturing by the manufacturing apparatus is necessary.

2. The support system according to claim 1, further comprising:
    a shaping device configured to shape the medical instrument;
    wherein the presentation unit; when presenting the shape suitable for the operation, presents whether shaping work by the shaping device is necessary; and
    the shaping device is configured to performs shaping of the medical instrument when the presentation unit presents that shaping by the shaping device is necessary.

3. The support system according to claim 1, wherein the presentation unit is configured to present a basis of presentation together with a content of the presentation.

4. The support system according to claim 1, wherein the use form of the medical instrument includes one or more of a shape, dimensions, hardness, a presence or an absence of a coating, and combinations of the shape, the dimensions, the hardness, and the presence or absence of the coating on the medical instrument.

5. The support system according to claim 1, wherein the machine learning is a supervised learning algorithm, an unsupervised learning algorithm, or a reinforcement learning algorithm.

6. The support system according to claim 1, wherein the medical instrument has a structure that can be shaped, and wherein the medical instrument is a guide wire, a guiding catheter, a catheter, or a microcatheter.

7. The support system according to claim 1, wherein the operation is performed using a surgical robot, and the use form of the medical instrument is configured in accordance with product specifications of the surgical robot.

8. A support method configured to present a medical instrument to be used for an operation to a health care worker, the method comprising:
    acquiring health care worker data on the health care worker, medical institution data on a medical institution, patient data on a patient, and operation data on a past operation experience of the health care worker;

performing machine learning using the health care worker data, the medical institution data, the patient data, and the operation data;

presenting a medical instrument recommended for use in operation on the patient and a recommended use form of the medical instrument based on a result of the machine learning;

presenting a shape of the medical instrument suitable for the operation when the medical instrument has a structure that can be shaped before the operation; and wherein the presenting of the shape suitable for the operation further comprises:

presenting whether a manufacturing work by a manufacturing apparatus is necessary, the manufacturing apparatus being configured to manufacture the medical instrument; and executing the manufacturing of the shaped medical instrument with the manufacturing apparatus when the presentation unit presents that the manufacturing by the manufacturing apparatus is necessary.

9. The support method according to claim 8, wherein when the presenting the shape suitable for the operation, the method comprising:

presenting whether shaping work by a shaping device is necessary, and wherein the shaping device is configured to shape the medical instrument; and shaping the medical instrument with the shaping device when the presentation unit presents that shaping by the shaping device is necessary.

10. The support method according to claim 8, further comprising:

presenting a basis of presentation together with a content of the presentation.

11. The support method according to claim 8, wherein the use form of the medical instrument includes one or more of shape, dimensions, hardness, a presence or an absence of a coating, and combinations of the shape, the dimensions, the hardness, and the presence or absence of the coating on the medical instrument.

12. The support method according to claim 8, wherein the machine learning is a supervised learning algorithm, an unsupervised learning algorithm, or a reinforcement learning algorithm.

13. The support method according to claim 8, wherein the medical instrument has a structure that can be shaped, and wherein the medical instrument is a guide wire, a guiding catheter, a catheter, or a microcatheter.

14. The support method according to claim 8, further comprising:

using a surgical robot to perform the operation; and configuring the use form of the medical instrument in accordance with product specifications of the surgical robot.

15. A non-transitory computer readable medium (CRM) storing computer program code executed by a computer processor that executes a process of presenting a medical instrument to be used for an operation to a health care worker, the process comprising:

acquiring health care worker data on the health care worker, medical institution data on a medical institution, patient data on a patient, and operation data on a past operation experience of the health care worker;

performing machine learning using the health care worker data, the medical institution data, the patient data, and the operation data;

presenting a medical instrument recommended for use in operation on the patient and a recommended use form of the medical instrument based on a result of the machine learning;

presenting a shape of the medical instrument suitable for the operation when the medical instrument has a structure that can be shaped before the operation; and wherein the presenting of the shape suitable for the operation further comprises:

presenting whether a manufacturing work by a manufacturing apparatus is necessary, the manufacturing apparatus being configured to manufacture the medical instrument; and executing the manufacturing of the shaped medical instrument with the manufacturing apparatus when the presentation unit presents that the manufacturing by the manufacturing apparatus is necessary.

16. The non-transitory computer readable medium according to claim 15, wherein when the presenting the shape suitable for the operation, the method comprising:

presenting whether shaping work by a shaping device is necessary, and wherein the shaping device is configured to shape the medical instrument; and shaping the medical instrument with the shaping device when the presentation unit presents that shaping by the shaping device is necessary.

17. The non-transitory computer readable medium according to claim 15, further comprising:

presenting a basis of presentation together with a content of the presentation.

* * * * *